United States Patent [19]

Ricks et al.

[11] Patent Number: 4,784,162

[45] Date of Patent: Nov. 15, 1988

[54] PORTABLE, MULTI-CHANNEL, PHYSIOLOGICAL DATA MONITORING SYSTEM

[75] Inventors: Robert D. Ricks, Newark; Robert Bornn, San Francisco; David B. Hurt, Mountain View, all of Calif.

[73] Assignee: Advanced Medical Technologies, San Mateo, Calif.

[21] Appl. No.: 910,457

[22] Filed: Sep. 23, 1986

[51] Int. Cl.$^4$ .................................. A61B 5/02
[52] U.S. Cl. ......................... 128/903; 128/668
[58] Field of Search .............. 128/903, 671, 782, 774, 128/731, 733, 668

[56] References Cited

U.S. PATENT DOCUMENTS 3,815,109  6/1974  Carraway et al. ................. 128/903

OTHER PUBLICATIONS

Acitvity Sensors for Use in Psychiatric Evaluation, R. McPartland et al., IEEE Trans. on Bio Medical Eng., Mar. 1976.
Telemetry Instrumentation for Kinosiologic Studies of Knee Motion, D. Foster et al., Apr. 1980, Med Research Eng.

Primary Examiner—Francis J. Jaworski
Assistant Examiner—George Manuel
Attorney, Agent, or Firm—Limbach, Limbach & Sutton

[57] ABSTRACT

A data monitoring system which simultaneously monitors, transmits by radio and records data relating to a plurality of physiological parameters comprises a portable sensor unit which is worn by the patient and includes a plurality of sensors attached to the patient's body each of which monitors a physiological parameter and generates a corresponding electrical signal, a circuit pack which converts the signals into a series stream of digital data and a transmitter which periodically transmits the data. A base station includes both a receiver which receives the transmitted data and reconverts it to a digital signal and a data processing unit which records the data.

8 Claims, 9 Drawing Sheets

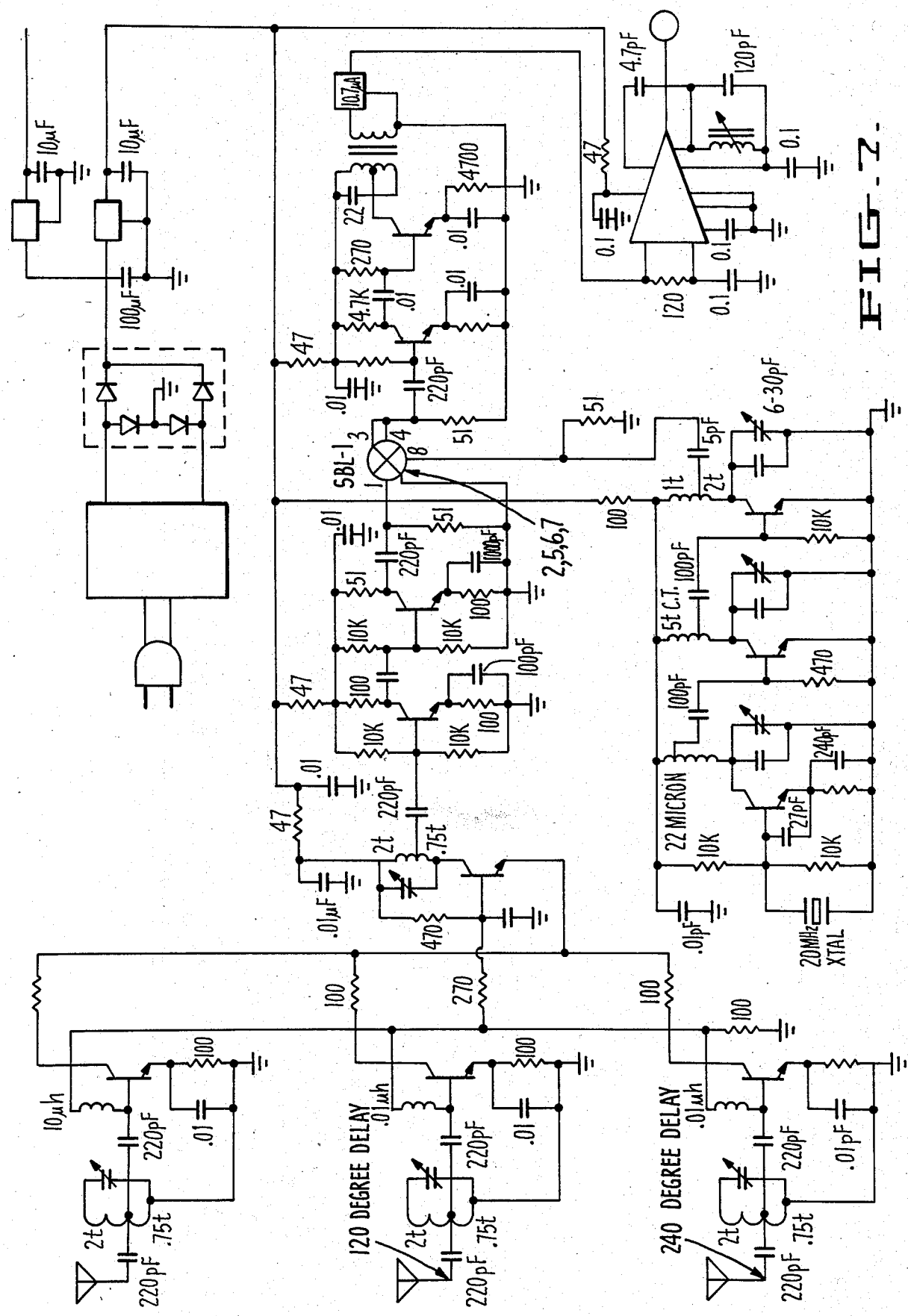

PORTABLE, MULTI-CHANNEL, PHYSIOLOGICAL DATA MONITORING SYSTEM

BACKGROUND OF THE INVENTION

1. Field of the Invention

The present invention relates to medical monitoring systems and, in particular, to a highly portable, non-invasive, physiological data telemetry recording system for monitoring sleep disorders.

2. Discussion of the Prior Art

Conventional practice for diagnosing sleep disorders requires that the patient be admitted to a "sleep lab". Typically, these sleep labs are located at hospitals or clinics and consist of a special in-patient unit equipped with a complicated array of cumbersome polysomnograph equipment. The patient is required to sleep in the unit while being monitored by a combination of bulky, uncomfortable sensors which are attached to various parts of the body. Obviously, the accuracy of the data generated under these circumstances is suspect because of the unfamiliar environment and physically uncomfortable circumstances in which the data is taken.

To eliminate the problems associated with "sleep labs", solid-state portable physiological monitoring systems have been developed for use in the patient's own environment.

One such system is available from Vitalog Corporation. The Vitalog system is a portable microcomputer which monitors information from up to eight physiological sensors. This information is processed and stored in on-board, solid-state memory for subsequent retrieval or display by a separate computer system.

The Vitalog system contains an eight-channel analog-to-digital interface and an R-wave detector. The multi-channel A/D converter samples eight analog inputs. A one-channel motion sensor composed of an array of omnidirectional mercury tilt switches detects patient movement. A one-channel electrocardiogram (ECG) signal is monitored using three standard ECG electrode pads. The amplified ECG signal is connected to an A/D channel and also to the R-wave detection circuit. A temperature sensor array monitors three channels of temperature using standard probes. Either one or two channels of respiration may be monitored. One channel can be programmed to monitor a patient response button.

When the Vitalog system is activated, its ROM-based operating system continuously monitors the sensor inputs. After each programmed monitoring period, information relating to heart rate, physical activity and temperature is stored. A running mean of normal R-R intervals is calculated at the end of each heart beat. At the end of each monitoring period, the current mean is encoded into one of 16 levels (4 bits) and stored. A filtered output count from the motion sensor is accumulated and encoded into one of 8 levels (3 bits). Temperature information is encoded using a 3-bit tracking scheme.

The Vitalog system can store data from a minimum of 3600 epochs. Data compression is used to ensure that no memory is used when data is unchanging.

A fundamental shortcoming of the Vitalog system is that it lacks individual event resolution. That is, because data gathered over a full monitoring period must be stored in limited on-board memory for retrieval at the end of the monitoring period, the data must be compressed prior to storage. This requires pre-storage processing according to a predefined algorithm, further limiting the stored data characteristics to rigid identifying and modifying signatures, thus reducing analytical flexibility.

Thus, while the Vitalog system provides a screening tool, it does not address the need for a low cost, reliable, portable physiological data recording system which provides high data resolution for a number of parameters over long periods of time.

SUMMARY OF THE INVENTION

It is an object of the present invention to provide a low-cost, miniature, portable, physiological data monitoring system.

It is also an object of the present invention to provide a portable, physiological data monitoring system which will simultaneously monitor, transmit by radio and continuously record a virtually unlimited quantity of data relating to a plurality of physiological parameters.

It is a further object of the present invention to provide a physiological data recording system with high frequency data gathering capability for high individual event resolution.

These and other objects of the invention are accomplished by the physiological data monitoring system of the present invention which consists of a portable sensor unit which is worn by the patient to continuously gather and transmit data and a base station which stores the transmitted data for review and analysis.

The portable sensor unit includes a plurality of sensors, each of which monitors a physiological parameter and generates a corresponding electrical signal. In the preferred embodiment of the invention, the following parameters are monitored: left and right abdominal ECG, vertical position, rotational movement, patient activity level, breath sound, chest respiration and abdominal respiration; a nurse call button is also provided. The signal from each sensor is converted to a serial stream of digital data which is transmitted in real time as a low level radio signal by a digital telemetry transmitter.

The system base station includes a digital telemetry receiver which picks up the transmitted radio signal and provides it as digital data to a processing system for storage. In addition to high capacity memory, the base station also includes a standard I/O port for communication with other systems for review and analysis of the data.

BRIEF DESCRIPTION OF THE DRAWINGS

FIG. 7 is a schematic diagram illustrating the circuitry of the telemetry receiver used in the system of the present invention.

DETAILED DESCRIPTION OF A PREFERRED EMBODIMENT

Figure 1:
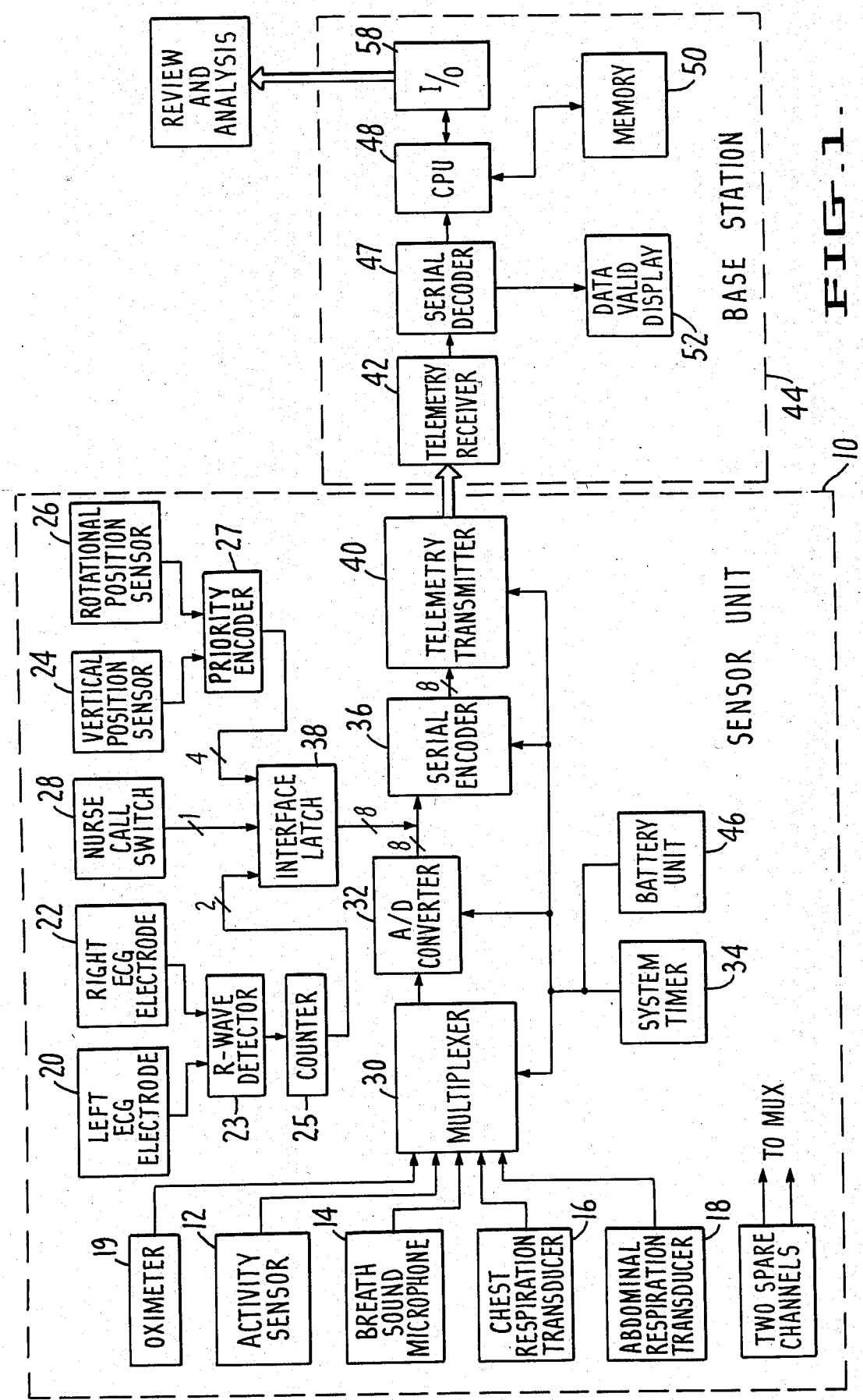
FIG. 1 is a schematic block diagram illustrating the system of the present invention.

FIG. 1 shows a schematic block diagram of the monitoring system of the present invention.

A portable sensor unit 10, which is worn by the patient to be monitored, includes a number of sensors which continuously gather physiological data from the patient and generate corresponding electrical signals.

In the embodiment shown in FIG. 1, the physiologic data sensors include: an activity sensor 12, a breath-sound microphone 14, a chest respiration transducer 16, an abdominal respiration transducer 18, an oximeter 19, left and right electrocardiogram (ECG) electrodes 20 and 22, respectively, a vertical position sensor 24 and a rotational movement sensor 26. The sensor unit 10 also includes a manually operated, nurse call switch 28. The embodiment of the invention described herein also includes two spare sensor channels which could be used to monitor additional physiological parameters, but are presently used to provide warning signals indicating low battery power and an ECG "leads-off" condition, as described below.

The electrical signals generated by activity sensor 12, breath-sound microphone 14, the two respiration sensors 16 and 18 and oximeter 19 are analog signals which are provided to a multiplexer 30. Multiplexer 30 sequentially forwards these signals, together with the signals from the two spare channels, to an analog-to-digital converter 32 in response to clock signals provided by a system timer 34. The A/D converter 32 converts the analog input signal from the sensors to a binary data word which serves as the input to a serial encoder 36.

The signals from the left and right ECG electrodes 20 and 22 are provided to an ECG and R-wave detector 23. The output of R-wave detector 23, which is representative of the patient's heart beat rate, is provided to a counter 25 which generates a 2-bit heart beat signal to interface latch 38. The signals from vertical position sensor 24 and rotational movement sensor 26 are provided to a priority encoder 27 which provides a 4-bit signal representative of these parameters to interface latch 38, the signal from the vertical position sensor 24 being given priority. Nurse call switch 28 provides a 1-bit "on-off" signal to latch 38.

The 8-bit output of interface latch 38 comprises 7 bits of data from its just-described associated sensors and an additional system synchronization bit, set to 1, to inform the base station 44 of the beginning of a transmission sequence. The 8-bit output of A/D converter 32 also includes 7 data bits from its associated channels, the eighth bit being always set to zero to distinguish it from the synchronization bit of the interface latch output.

Serial encoder 36 converts each of the 8-bit parallel digital signals from A/D converter 32 and interface latch 38 to a serial data stream. The serial data stream is then provided to a digital telemetry transmitter 40 which transmits the uncompressed data by low-power radio signals at one-half second intervals to a telemetry receiver 42 of portable base station 44.

Thus, the complete transmission sequence is composed of eight channels, each 8 data bits wide, as described above. Each channel is composed of 12 synchronization pulses, a 7-bit address which identifies the channel and the 8 data bits.

The power for the sensor unit 10 is provided by a battery unit 46, which comprises four AAAA size batteries of 0.3" thickness. Use of these "quad-A" batteries allows the thickness of sensor unit 10 to be less than about 0.5 inches, making it relatively inobtrusive in comparison to prior art devices.

The radio signal received by telemetry receiver 42 is provided as a digital signal to CPU 48 which stores the data in memory 50 and/or communicates with additional peripheral devices via I/O port 58 for review and analysis of the data. The base station 44 also includes an LED display which verifies that data is being received and stored.

Figure 2:
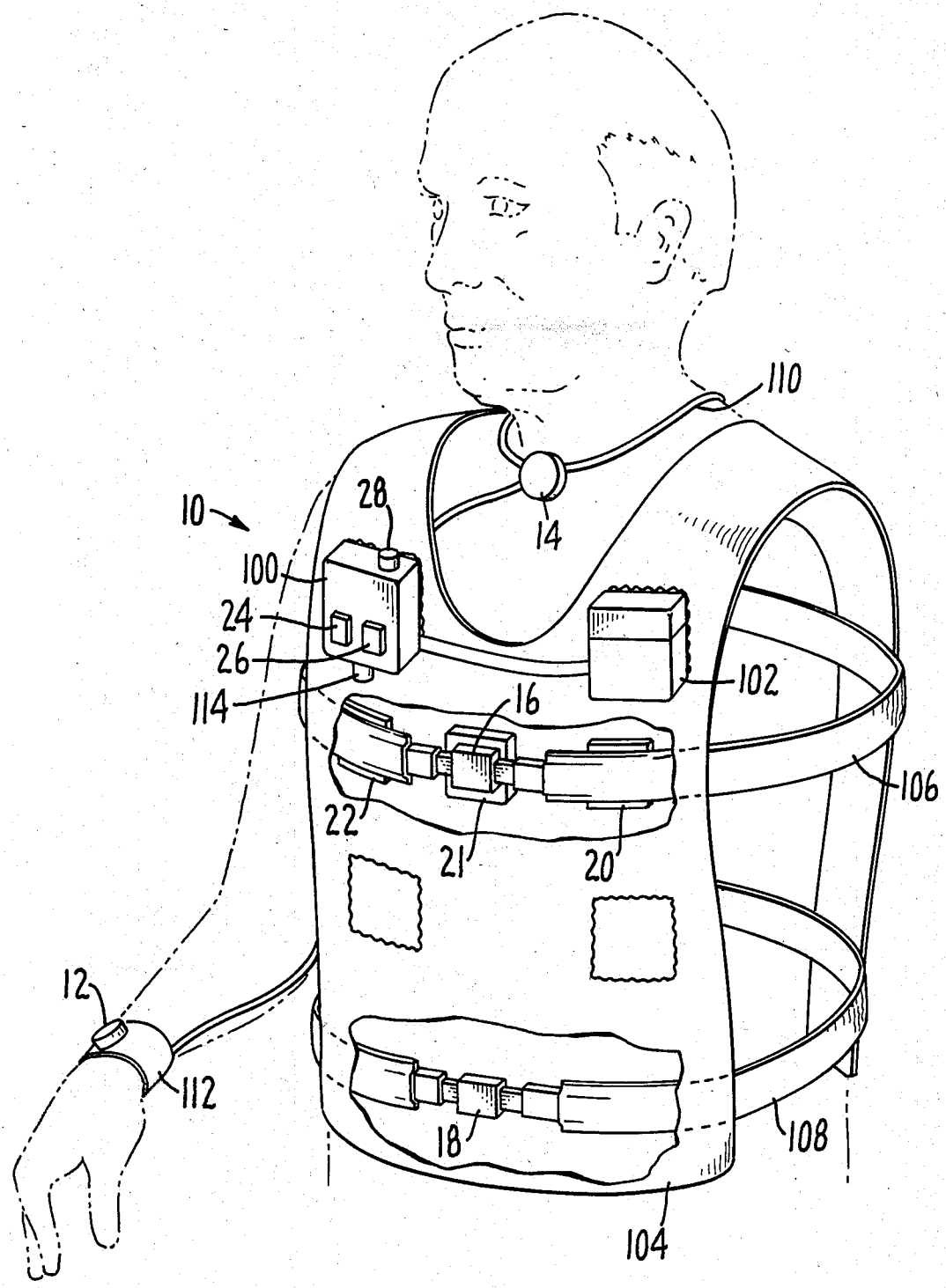
FIG. 2 is an illustration of the sensor unit of the system of the present invention.

As shown in FIG. 2, sensor unit 10 includes a hybrid analog/digital circuit pack 100 which receives signals from the various sensors described above and provides these signals as a serial digital data stream to a second pack 102 which includes battery unit 46 and telemetry transmitter 40.

The circuit pack 100 and the battery/transmitter pack 102 are both attached to a body vest 104 by means of a Velcro ® patch attached to the back of each unit 100, 102 and a corresponding patch attached to the vest 104. The vest 104 includes Velcro ® patches for this purpose located both at the upper chest portion and at the abdominal portion so that the patient may attach the two packs 100 and 102 at the personally most comfortable location.

The hybrid circuit pack 100 receives the two respiration signals from two conventional respiration transducers 16 and 18 which are mounted around the patient's chest and abdomen, respectively. As shown in FIG. 2, each of the chest and abdominal respiration transducers 16 and 18 is formed as part of a body strap 106 and 108, respectively, which fits around the patient's torso to position the transducer at the desired location.

Two ECG electrodes 20 and 22 are attached to the patient, one at each side of the patient's chest area, and connected by shielded leads to the hybrid circuit pack 100. A third ground ECG electrode 21 is attached to the patient between the other two. In the preferred embodiment, the three ECG electrodes 20, 21 and 22 are connected to the inner side of chest respiration strap 106.

An electret microphone 14 is located at the patient's suprasternal notch by means of a throat collar 110. Microphone 14 monitors the patient's breath sound and transmits a representative signal to the hybrid circuit pack 100.

A vibration piezo transducer 12 mounted on the patient's wrist by means of a bracelet 112 also provides its signal to the hybrid circuit pack 100.

The hybrid pack 100 further includes two position sensors 24 and 26 which, in the preferred embodiment, are mercury switches which monitor rotational movement and vertical position, respectively. A position switch 114 mounted at the bottom of the hybrid circuit box is used to normalize the body position of the patient when the position switch 114 is pressed. That is, when the position switch 114 is pressed, the patient's position at that time is defined as being "nose up", i.e., the patent is on his back with his nose in the vertical position. A nurse call button 28 is located at the top of the hybrid circuit pack 100 and may be activated by the patient.

Figure 3A:
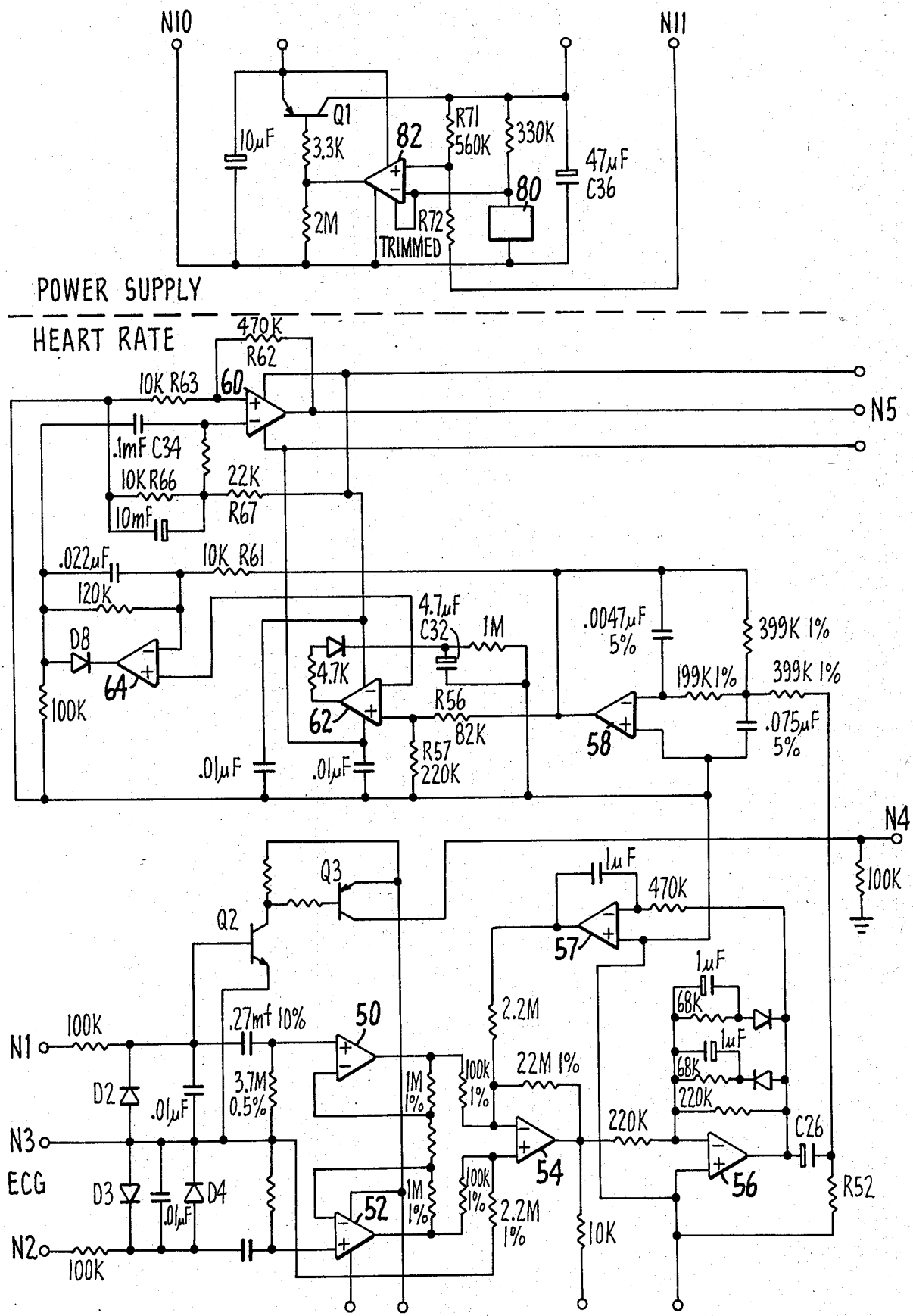
FIGS. 3A and 3B combine to provide a schematic circuit diagram illustrating the analog portion of the sensor unit circuit of the system of the present invention.
Figure 3B:
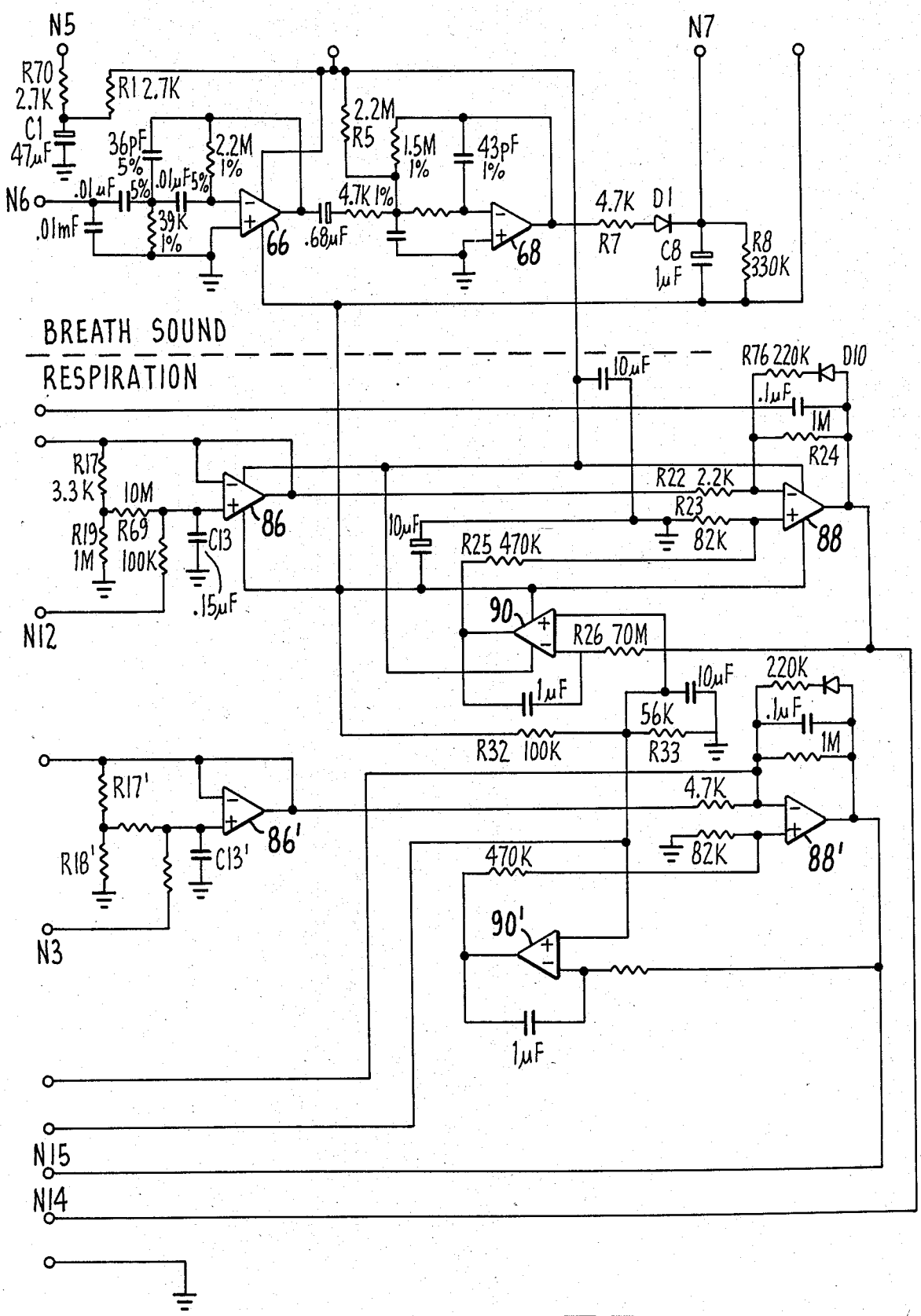

FIGS. 3A and 3B provide a detailed circuit schematic diagram of the analog portion of sensor unit 10.

As shown in FIG. 3A, nodes N1 and N2 receive the left and right ECG signals, respectively, from left and right ECG electrodes 20 and 22 for the Heart Rate portion of the circuit. Node N3 is connected to center ECG/ground electrode 21. The ECG inputs from nodes N1 and N2 are provided to components 50 and 52, respectively, which together with component 54 form an instrumentation amplifier with a gain of approximately 1000. Transistors Q2 and Q3 form a "leads-off" detector circuit, where the base/emitter junction of transistor Q2 forms a fourth diode with clamping diodes D2, D3 and D4. This "leads-off" detector circuit operates with an external bias such that the conducting path is either from node N1 to ground node N3 or from node N1 to node N2 with the ECG leads connected. With the leads off, the current from ECG electrode 20 which is connected to node N1, is provided to the base of transistor Q2. This turns on both transistor Q2 and transistor Q3 and provides a high level output at node N4. This output is provided to one of the unused transmission channels, as mentioned above, to indicate that an ECG lead is disconnected.

A gain block composed of instrumentation amplifier 56, together with its feedback component, form a limiting amplifier with amplitude and slew rate limiting. The output of instrumentation amplifier 56 is zeroed by an autonull amplifier 57 which assures that the output of instrumentation amplifier 56 is forced quiescently toward zero. The output of instrumentation amplifier 56 is provided to a high pass formed by capacitor C26 and resistor R52 and also to a band pass filter 58. The output of band pass filter 58 is provided to a resistor divider formed by resistors R56 and R57 to ground and also to resistor R61 which is an input of amplifier 64. Amplifier 62 and its feedback circuitry receive the information from the output of amplifier 58 and capture that peak voltage onto capacitor C32. The voltage of capacitor C32 is then applied to the positive input of amplifier 64, the other input to amplifier 64 being provided through previously-mentioned resistor R61. The output of amplifier 64 through polarity blocking diode D8 forms a negative going waveform, which is the difference between the peak voltage applied at the positive input to amplifier 64 and the output of amplifier 58, and is applied through capacitor C34 to a comparator 60, the threshold of which is set by a divider provided by resistor R67 through resistor R66 to ground. Resistors R62 and R63 form positive feedback, or hysteresis, to assure clean switching of the output. The output of comparator 60 is then provided to node N5 which is the output pin of the Heart Rate, or ECG, circuit and the input to heart rate counter 25 shown in FIG. 1. The total of this aforedescribed circuitry forms R-wave detector 23 which provides one pulse per peak electrical QRS complex.

Referring now to the Breadth Sound section of FIG. 3B, resistor R1, capacitor C1 and resistor R70 form a bypass and bias network for electret microphone 14, the network then being connected back to node N6 of the circuit. The network around amplifier 66 forms a gain block and band pass filter which feeds a second gain block and band pass filter 68. The band pass of this network is approximately 300-900 Hz, while the network gain is approximately 500. The output of filter 68 is biased by resistor R5 toward the negative rail to allow full scale presentation of the breadth sound signal amplitude. This output is applied to resistor R7 and through diode D1. The peak waveform is captured across capacitor C8 to the negative rail with the discharge path through resistor R8 and parallel with capacitor C8 to output node N7 which is an input to multiplexer 30.

Figure 4:
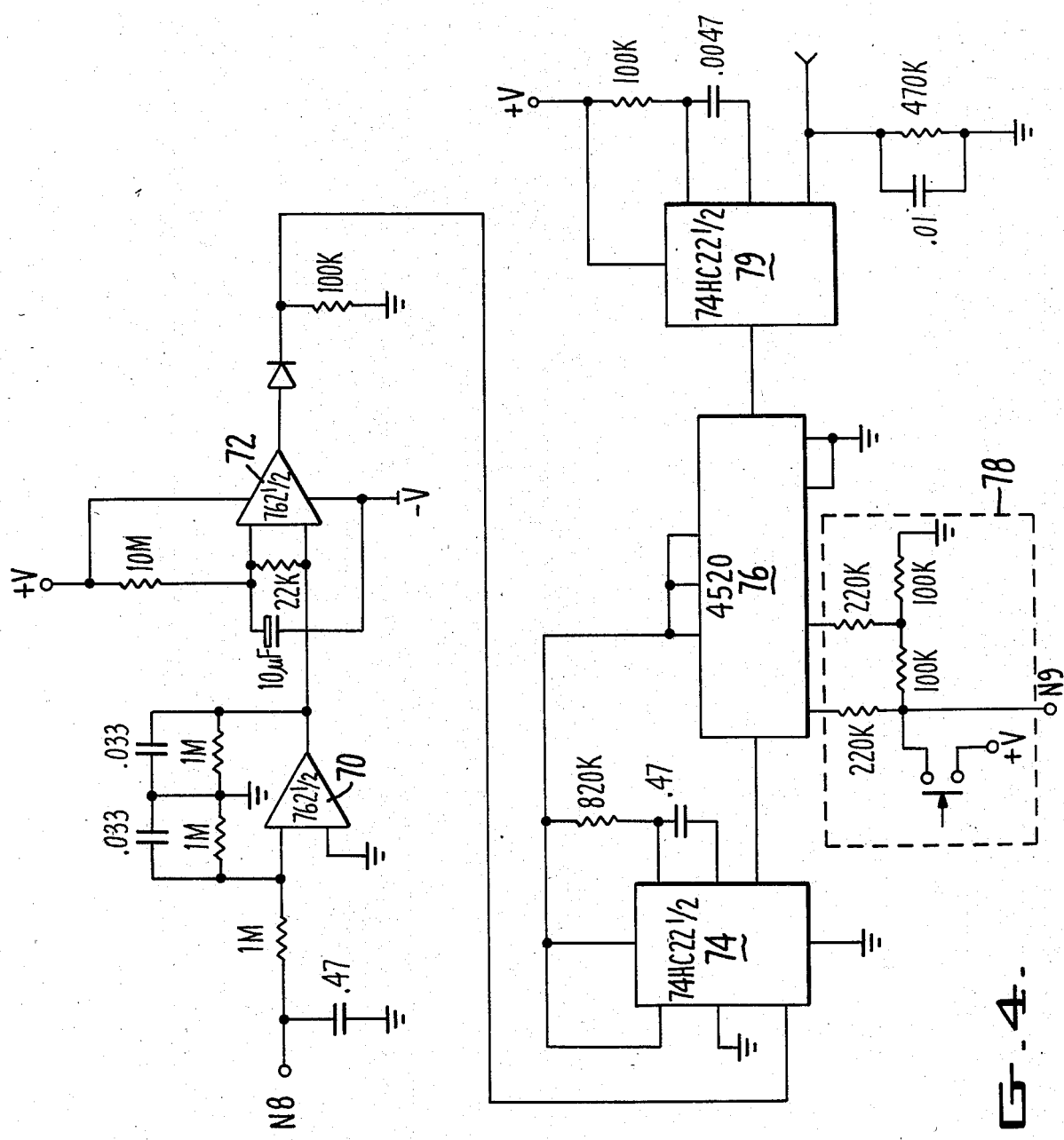
FIG. 4 is a schematic circuit diagram illustrating the activity sensor portion of the sensing unit circuit of the system of the present invention.

Referring now to FIG. 4, which shows the Activity portion of the circuit, the signal from the activity transducer 12 is received at node N8, provided to amplifier and low pass filter 70 and then to tracking comparator 72. The output of tracking comparator 72 is provided to non-retriggerable one-shot 74 which clocks out a digital signal to counter 76. The output of counter 76 is provided to a digital-to-analog converter 78, the output node N9 of which serves as an input to multiplexer 30. The counter 76 is reset to the 0 position by non-retriggerable one-shot 79 which is triggered by the falling edge of the transmitter enable signal, as described below.

Referring now to the Power Supply section of FIG. 3A, a 1.2 reference voltage 80 is provided to the negative input of amplifier 82. Transistor Q1, which is a series pass element, is operated in the inverted mode for low dropout characteristic. The feedback path for the regulator is through resistors R71 and R72 where nodes N10 and N11 are tied together for this application. Capacitor C36 forms an output compensation network to provide stability, since transistor Q1 is operating as a gain stage. Resistor R15 provides start-up current for the regulator.

Referring now to the Respiration section of FIG. 3B, the signals from both the abdominal and the chest transducers 18 and 16 are received at nodes N12 and N13, respectively. The signal received at node N12 is applied to capacitor C13 and to a boot strap amplifier 86 formed by booting resistors R17 and R19 to ground, where resistor R69 is brought off the center of this bootstrap configuration and provides a thousand megohm equivalent inputted impedance. The output of bootstrap amplifier 86 is applied through a gain block 88, the gain of which is set by resistors R22 and R24. The output of amplifier 88 is provided past one diode drop and again is reduced by the forward conductivity of diode D10, putting resistor R76 in parallel with resistor R24. Amplifier 90 and its associated circuitry provide an autonull loop for the output of bootstrap amplifier 88 which is sensed through resistor 26. The output of amplifier 90 is coupled back into amplifier 88 through resistor R25. The quiescent voltage of amplifier 88 is set by resistor divider R32 and R33 and is approximately −1.1 volts. Thus, the output of the abdominal transducer potion of the circuit is provided at node N14.

The chest transducer signal received at node N13 is similarly processed via amplifiers 86′, 88′ and 90′ to provide a chest transducer output at node N15.

Figure 5A:
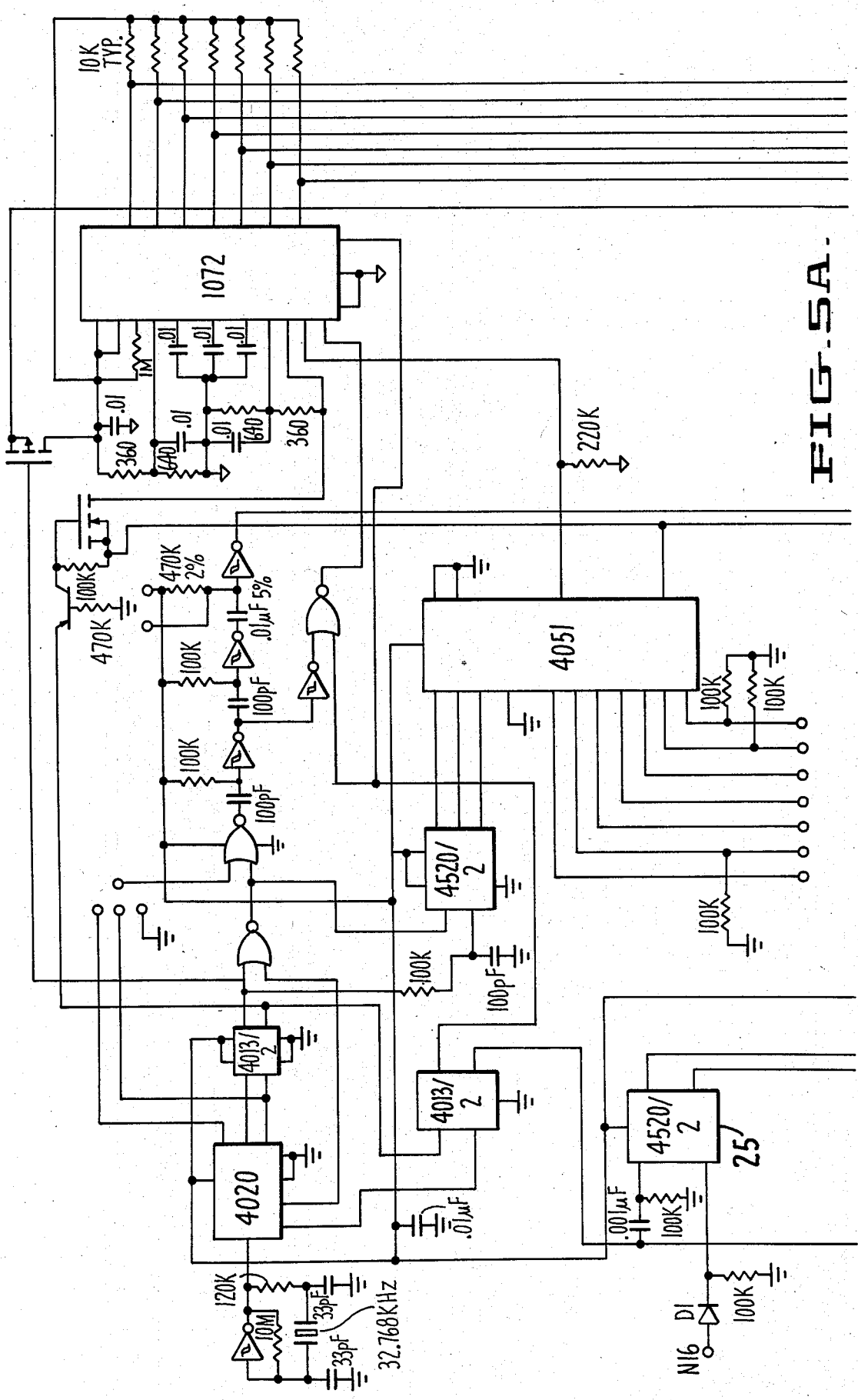
FIGS. 5A and 5B combine to provide is a schematic circuit diagram illustrating the digital portion of the sensing unit circuit of the system of the present invention.
Figure 5B:
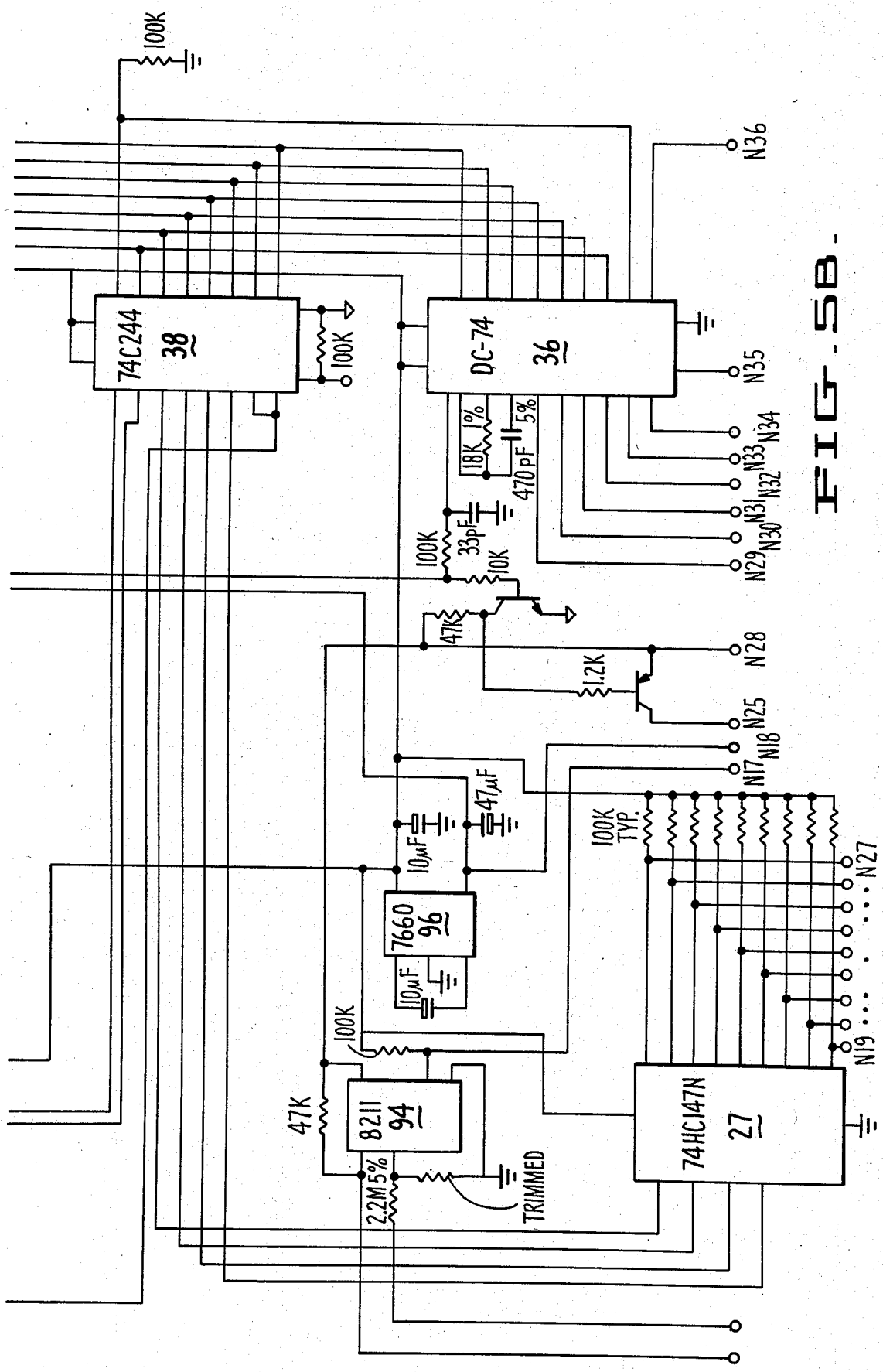

Referring now to the digital portion of the sensor unit circuitry shown in FIGS. 5A and 5B, the output of the Heart Rate circuitry of FIG. 3A is provided to node N16 and passes through diode D1 which shifts the level from positive to negative voltage. The logic requires only a positive to ground; therefore, diode D1 blocks the negative voltage and 4-bit counter 25 stores the heart rate count. This information is then provided to interface latch 38 as a 2-bit signal every one-half second during transmission.

A low voltage battery detector 94 provides its output on node N17 to one of the otherwise unused analog channels mentioned above. A low battery is, therefore, detected at base station 44.

A voltage converter 96 receives the voltage from the battery unit 46 and converts it to a negative voltage output. Therefore, node N18 of the digital hybrid circuit is the −4.5 voltage negative power supply point for the system.

Priority encoder 27 receives the signals from both position sensors 24 and 26, with the vertical position transducer receiving highest priority, and encodes it into four bits of binary weighted code. Nodes N19–N27 are the input pins from the position transducers.

Node N28 of the digital hybrid circuit switches the transmitter power supply and is gated from the output of the system enable timer 34. Thus, the signal at node N28 resets the one-shot 79 of the activity circuit.

Serial encoder 36 receives parallel digital data presented on its input pins and applies a serial output to the channel address at nodes 29–35, bringing these nodes either to ground or to the positive rail. Serial encoder 36 also produces an 8-bit serial data stream at node N36 which modulates transmitter 40.

Interface latch 38 switches in the digital information from its associated sensors during the digital channel transmission.

A/D converter 32 receives the output of analog multiplexer 30 and, upon command, digitizes each of the analog levels presented by multiplexer 30.

Transistors Q4 and Q5 are gated power supply devices which provide power to A/D converter 32.

Figure 6:
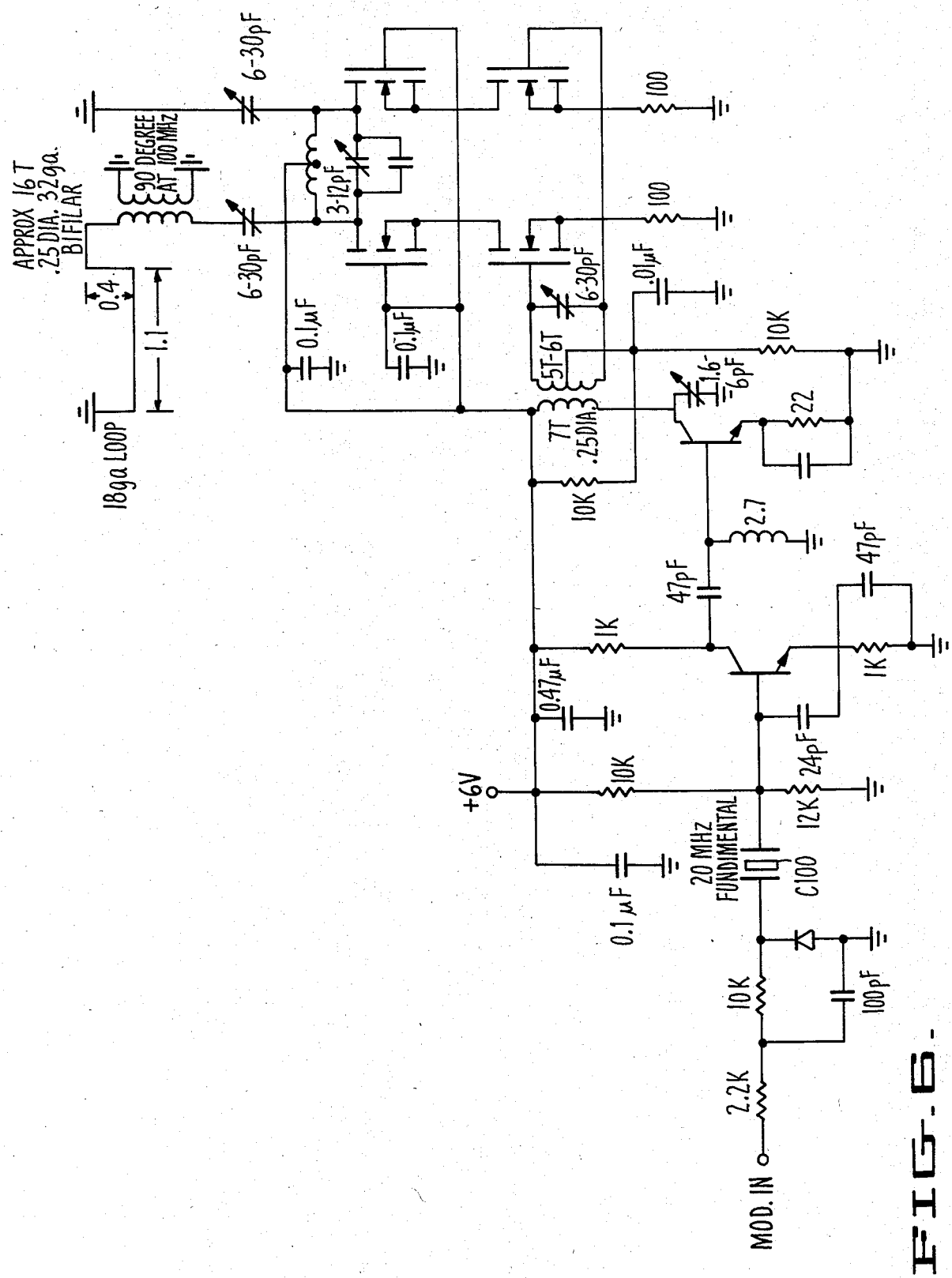
FIG. 6 is a schematic diagram illustrating the circuitry of the telemetry transmitter used in the system of the present invention.

FIG. 6 shows a detailed schematic circuit diagram of the digital telemetry transmitter 40.

As shown in FIG. 6, the serial data transmissions from encoder 36 are first modulated by a programmable data coder and then provided to a low pass filter. The filtered signals are then provided to a modulator, the output of which is forwarded to an oscillating section of the transmitter circuitry, the frequency determining element of which, i.e., crystal C100, has a resonant frequency of approximately 20 MHz. The outputs of the crystal C100 are amplified before exiting the oscillator section of the circuit and then forwarded to a first frequency tripler which triples the third harmonic of the oscillator output. The output of the first frequency tripler section is provided to a second frequency tripler section which generates the ninth harmonic of the oscillator output. The frequency of the output of the second tripler section is in the range of 180–212 MHz, which is known as the medical band. The outputs of the second tripler section are forwarded to the antenna elements of the transmitter 40 for transmission to the base station 44.

FIG. 7 shows a detailed schematic circuit diagram of the digital telemetry receiver 42. The signals transmitted from the transmitter 40 are received by the antenna elements of receiver unit 42. The signals received by the antenna elements are forwarded to an amplifier and summer network. The outputs of this network are forwarded to an RF amplifier, a mixer, and an amplifier and filter section. The output of the amplifier and filter section is provided to a serial decoder 47 which outputs an 8-bit digitized audio signal that is provided to CPU 48 for either storage in memory 50 or transmission through I/O port 58 to diagnostic equipment for analysis and review.

In the preferred embodiment, CPU 48 is an Hitachi 64180 microprocessor which directly addresses 512K of RAM and has a built-in R232C I/O port.

Data valid display 52 is an LED which is driven from a one-shot which is triggered by the data-valid port of serial decoder 47.

It should be understood that various alternatives to the embodiment shown herein may be employed in practicing the present invention. It is intended that the following claims define the invention, and that the structure within the scope of these claims and their equivalents be covered thereby.

What is claimed is:

1. A data monitoring system for gathering physiological data from a subject, the system comprising
   (a) a portable sensing unit comprising
      (i) a first plurality of sensors, each of the sensors of the first plurality being adapted for attachment to the subject for monitoring the value of a physiological parameter of the subject and for generating a signal corresponding to that value;
      (ii) a multiplexer which receives the analog signals from the first plurality of sensors and sequentially forwards the analog signals to an analog-to-digital converter;
      (iii) an analog-to-digital converter which receives the sequentially forwarded analog signals from the multiplexer as an input signal and converts the input signal to a corresponding first binary data word which is provided in parallel to a serial encoder;
      (iv) a second plurality of sensors, each of the sensors of the second plurality being adapted for attachment to the subject for monitoring the value of a physiological parameter of the subject and for generating an electrical signal corresponding to that value;
      (v) means for converting the electrical signals generated by the second plurality of sensors into a corresponding second binary data word which is provided in parallel to the serial encoder;
      (vi) a serial encoder which receives the first and second binary data words and converts them to a serial digital data stream; and
      (vii) a digital telemetry transmitter which receives the serial digital data stream and transmits the serial digital data stream by low-power radio signals; and
   (b) a base station comprising
      (i) a receiver which receives the radio signal and reconverts it to a digital data signal; and
      (ii) a data processing unit which receives the reconverted digital data signal for storage and/or analysis and review.

2. A data monitoring system as in claim 1 wherein the first binary data word includes at least one bit which identifies the first word as corresponding to the first plurality of sensors, and wherein the second binary data word includes at least one bit which identifies the second word as corresponding to the second plurality of sensors.

3. A data monitoring system as in claim 1 wherein the digital data stream is transmitted uncompressed.

4. A data monitoring system as in claim 1 wherein the second plurality of sensors includes means for generating a signal corresponding to the subject's heart rate, comprising
   (a) ECG electrode means attached to the subject for developing an electrical signal corresponding to the subject's heart rate;
   (b) an R-wave detector responsive to the electrical signal from the ECG electrode means to provide one pulse per peak electrical QRS complex; and
   (c) a counter which monitors the pulsed output of the R-wave detector and provides a corresponding binary signal to the electrical signal conversion means.

5. A data monitoring system as in claim 1 wherein the second plurality of sensors includes means for sensing body position of the subject comprising
   (a) a first body position transducer which generates an output corresponding to the vertical position of the subject;
   (b) a second body position transducer which generates an output corresponding to the rotational position of the subject; and
   (c) a priority encoder which receives the output from the first and second body position sensors, the output of the second transducer receiving highest priority, and provides a corresponding binary weighted output code to the electrical signal conversion means.

6. A data monitoring system as in claim 1 wherein the first plurality of sensors includes means for sensing breadth sound comprising
   (a) an electret microphone for generating a signal representative of the subject's breadth sound;
   (b) means responsive to the output of the electret microphone for full scale presentation of the breadth sound signal amplitude; and
   (c) a capacitor for capturing the peak wave form of the breadth sound signal, the discharge of the capacitor serving as an input to the multiplexer.

7. A data monitoring system as in claim 1 wherein the first plurality of sensors includes means for sensing subject activity comprising
   (a) an activity transducer for generating an output signal corresponding to the activity level of the subject;
   (b) means for comparing the activity transducer output signal with a reference signal and for providing a tracking signal corresponding to the difference between the output signal and the reference signal;
   (c) a non-retriggerable one-shot responsive to the tracking signal to clock out a corresponding digital signal; and
   (d) a counter which monitors the digital signal, the output of the counter being provided to the multiplexer via a digital-to-analog converter.

8. A data monitoring system as in claim 1 wherein the first plurality of sensors includes means for sensing the respiration of the subject comprising a respiratory transducer adapted for attachment to the subject's body, the output of the respiratory transducer being applied to a capacitor and boot strap amplifier, the output of the bootstrap amplifier being applied to a gain block having a predetermined gain, the output of the gain block being provided to the multiplexer via an autonull loop.

* * * * *